United States Patent
Romar Andres et al.

(10) Patent No.: US 11,208,622 B2
(45) Date of Patent: Dec. 28, 2021

(54) PROCESSING AND USE OF REPRODUCTIVE TRACT FLUIDS TO IMPROVE THE IN VITRO PRODUCTION OF MAMMALIAN EMBRYOS

(71) Applicant: Universidad de Murcia, Murcia (ES)

(72) Inventors: Raquel Romar Andres, Murcia (ES); Maria Pilar Coy Fuster, Murcia (ES)

(73) Assignee: UNIVERSIDAD DE MURCIA, Murcia (ES)

( * ) Notice: Subject to any disclaimer, the term of this patent is extended or adjusted under 35 U.S.C. 154(b) by 0 days.

(21) Appl. No.: 15/517,878

(22) PCT Filed: Oct. 7, 2015

(86) PCT No.: PCT/ES2015/070727
§ 371 (c)(1),
(2) Date: Apr. 7, 2017

(87) PCT Pub. No.: WO2016/055681
PCT Pub. Date: Apr. 14, 2016

(65) Prior Publication Data
US 2017/0313966 A1    Nov. 2, 2017

(30) Foreign Application Priority Data
Oct. 8, 2014   (ES) ................ ES201400811

(51) Int. Cl.
| | | |
|---|---|---|
| C12N 5/073 | (2010.01) | |
| C12M 3/00 | (2006.01) | |
| A61K 35/48 | (2015.01) | |
| A01K 67/02 | (2006.01) | |
| A61B 17/43 | (2006.01) | |
| B01L 3/00 | (2006.01) | |
| C12Q 1/02 | (2006.01) | |
| A01K 67/00 | (2006.01) | |
| C12M 1/00 | (2006.01) | |

(52) U.S. Cl.
CPC ............ *C12M 21/06* (2013.01); *A01K 67/02* (2013.01); *A61B 17/43* (2013.01); *A61K 35/48* (2013.01); *B01L 3/50* (2013.01); *C12N 5/0604* (2013.01); *C12Q 1/02* (2013.01); *A01K 67/00* (2013.01); *B01L 2200/06* (2013.01); *C12M 1/00* (2013.01); *C12N 2517/10* (2013.01)

(58) Field of Classification Search
None
See application file for complete search history.

(56) References Cited

U.S. PATENT DOCUMENTS

2013/0344595 A1   12/2013  Gardner et al.

FOREIGN PATENT DOCUMENTS

| CN | 103333855 A | 10/2013 |
|---|---|---|
| ES | 2323993 | 7/2009 |
| ES | 2439424 | 1/2014 |
| WO | 2006012177 A2 | 2/2006 |

OTHER PUBLICATIONS

Parrish et al, Capacitation of Bovine Spermatozoa by Oviduct Fluid, Biology of Reproduction, vol. 40, pp. 1020-1025 (1989).*
Henkel et al., Sperm preparation for ART, Reproductive Biology and Endocrinology, 2003, vol. 1:108, pp. 1-22.*
U.S. FDA, The Cattle Estrous Cycle and FDA-Approved Animal Drugs to Control and Synchronize Estrus, retrieved from the internet: www.fda.gov/animal-veterinary/product-safety-information/cattle-estrous-cycle-and-fda-approved-animal-drugs-control-and-synchronize-estrus-resource-producers (Year: 2020).*
Vet Tips, AI, Estrous Cycle, Embryo transfer in cattle, Synchronization protocols, and General Biotech, retrieved from the internet: www.vettips.org/ai-estrous-cycle-embryo-transfer-in-cattle-synchronization-protocols-and-general-biotech-illustrative-with-pics/ (Year: 2020).*
Ehrenwald et al., Molecular Reproduction and Development, vol. 25:195-204 (1990) (Year: 1990).*
Aitken, R.J., "The culture of mouse blastocysts in the presence of uterine flushings collected during normal pregnancy, delayed implantation and pro-oestrus", J. Embryol. exp. Morph, 1977, pp. 295-300, vol. 41, Great Britain, Company of Biologists Limited.
Alvarez et al. "Centrifugation of human spermatozoa induces sublethal damage; separation of human spermatozoa from seminal plasma by a dextran swim-up procedure without centrifugation extends their motile lifetime." Human Reproduction, Jul. 1993, pp. 1087-1092, vol. 8.7, Oxford University Press.
Aviles et al., "Oviductal secretions: will they be the key factors for the future ARTs?", Molecular Human Reproduction, May 2010, pp. 896-906, vol. 16.12, Advanced Access Publication.
Bo, G.A. and Mapletof, R.J., "Evaluation and classification of bovine embryos", Anim. Reprod., Jul./Sep. 2013, pp. 344-348, vol. 10.3, Argentina.
Carrasco, Luis et al., "Glycosidase determination in bovine oviducal fluid at the follicular and luteal phases of the oestrous cycle", Reproduction, Fertility, and Development, 2008, pp. 808-817, vol. 20, CSIRO Publishing.
Carrasco, Luis et al., "Determination of glycosidase activity in porcine oviductal fluid at the different phases of the estrous cycle", Reproduction, 2008, pp. 833-842, vol. 136,Society for Reproduction and Fertility.

(Continued)

*Primary Examiner* — Scott Long
*Assistant Examiner* — Evelyn Y Pyla
(74) *Attorney, Agent, or Firm* — Hayes Soloway P.C.

(57) ABSTRACT

Processing and use of fluids from the reproductive tract (biofluids) to improve the in vitro production of mammalian embryos comprising the following steps: a) fractionation and processing of biofluids through a sorting, purification, lyophilization and subsequent storage; b) a method of sperm capacitation in a culture medium supplemented with biofluids; c) in vitro fertilization in a medium enriched with biofluids and d) subsequent in vitro culture with development of the obtained embryos to any stage of preimplantational development in culture media supplemented with biofluids.

1 Claim, No Drawings

(56) References Cited

OTHER PUBLICATIONS

Cebrian-Serrano et al., "Effect of the Bovine Oviductal Fluid on In Vitro Fertilization,Development and Gene Expression of In Vitro-Produced Bovine Blastocysts", Reproduction in Domestic Animals, 2013, pp. 331-338, vol. 48, Blackwell Verlag GmbH.

Coy et al., "Oviduct-specific glycoprotein and heparin modulate sperm-zona pellucida interaction during fertilization and contribute to the control of polyspermy" PNAS, 2008, pp. 15809-15814, vol. 4, National Academy of Sciences of the USA.

Coy et al., "Hardening of the zona pellucida of unfertilized eggs can reduce polyspermic fertilization in the pig and cow" Reproduction, 2008, pp. 19-27, vol. 135, Society for Reproduction and Fertility.

Coy et al.,"Effects of porcine pre-ovulatory oviductal fluid on boar sperm function", Theriogenology, 2010, pp. 632-642, vol. 74, Elsevier.

Faulkner et al., "A comparison of the bovine uterine and plasma proteome using iTRAQ proteomics", Proteomics, 2012, pp. 2014-2023, vol. 12, WILEY-VCH Verlag GmbH & Co. KGaA, Weinheim.

Gapp et al., "Implication of sperm RNAs in transgenerational inheritance of the effects of early trauma in mice", Nature Neuroscience, May 2014, pp. 667-669, vol. 17.5, Author manuscript.

Garcia-Lopez et al., "Reversion of thermic-shockeffect on ram spermatozoa by adsorption of seminal plasma proteins revealed by partition in aqueous two-phase systems", Journal of Chromatography, 1996, pp. 137-143, vol. 680, Elsevier.

Hao et al., "Osteopontin Reduces Polyspermy During In Vitro Fertilization of Porcine Oocytes", Biology of Reproduction, 2006, pp. 726-733, vol. 75, Published online, https://doi.org/10.1095/biolreprod.106.052589.

Iritani et al., "Secretion Rates and Chemical Composition of Oviduct and Uterine Fluids in Sows", Journal of Animal Science, 1974, pp. 582-588, vol. 39, American Society of Animal Science.

Killian et al.,"Changes in phospholipids, cholesterol and protein content of oviduct fluid of cows during the oestrous cycle", J. Reprod. Fert., 1989, pp. 419-426, vol. 86, Journals of Reproduction and Fertility Ltd, Great Britain.

Leese et al., "Female reproductive tract fluids: composition, mechanism of formation and potential role in the developmental origins of health and disease", Reproduction, Fertility and Development, 2008, pp. 1-8,vol. 20, CSIRO Publishing.

Lippes and Wagh, "Human oviductal fluid proteins. VI. Correlation between alpha-fetoprotein and serum levels of ovarian hormones", Fertility and Sterility, 1993, pp. 157-162, vol. 69.1, The American Fertility Society.

Matas et al., "Effect of sperm preparation method on in vitro fertilization in pigs", Reproduction, 2003, pp. 133-141, vol. 125, Society for Reproduction and Fertility.

Meintjes et al., "A randomized controlled study of human serum albumin and serum substitute supplement as protein supplements for IVF culture and the effect on live birth rates", Embryology, 2009, pp. 782-789, vol. 24.4, Advanced Access Publication.

Menkveld et al., "Comparison of a discontinuous Percoll Gradient Method Versus A Swim-Up Method: Effects On Sperm Morphology and other Semen Parameters", andrologia, 1990, pp. 152-158, vol. 22.2, Blackwell Verlag GmbH.

Mondejar et al., "The human is an exception to the evolutionarily-conserved phenomenon of pre-fertilization zona pellucida resistance to proteolysis induced by oviductal fluid", Human Reproduction, 2013, pp. 1-11, vol. 0.0, Oxford University Press on behalf of the European Society of Human Reproduction and Embryology.

Petters and Wells, "Culture of pig embryos", Journal of Reproduction and Fertility Supplement, 1993, pp. 61-73, vol. 48, Journals of Reproduction and Fertility Ltd.

Rondeau et al., "Growth and Metabolism of Murine and Bovine Embryos in Bovine Uterine Flushing-Supplemented Culture Media", Canadian journal of veterinary research, 1996, pp. 14-20, vol. 60.

Velazquez et al.,"Sampling techniques for oviductal and uterine luminal fluid in cattle" Theriogenology, 2010, pp. 758-767, vol. 73, Elsevier.

Zini et al.,"Influence of semen processing technique on human sperm DNA integrity", Urology, 2000, pp. 1081-1084, vol. 56.6, Elsevier.

Li et al., "Development, Freezability and Amino Acid Consumption of Bovine Embryos Cultured in Synthetic Oviductal Fluid (SOF) Medium Containing Amino Acids at Oviductal or Uterine-Fluid Concentrations", Theriogenology 66, (2006) p. 404-414, Elsevier Inc.

Kim et al., "Effects of Oviductal Fluid on Sperm Penelralion and Cortical Granule Exocytosis During Fertilization of Pig Oocytes In Vitro", Journal of Reproduction and Fertility (1996) 107, p. 79-86, Society for Reproduction and Fertility.

Lloyd et al., "Effects of Oviductal Fluid on the Development, Quality, and Gene Expression of Porcine Blastocysts Produced In Vitro", Reproduction (2009) 137, p. 679-687, Society for Reproduction and Fertility.

Elhassan et al., "Amino Acid Concentrations in Fluids from the Bovine Oviduct and Uterus and in KSOM-Based Culture Media", Theriogenology 55, p. 1907-1918, Elsevier Science Inc., (2001).

N.J. Hannan et al.; "Analysis of Fertility-Related Soluble Mediators in Human Uterine Fluid Identifies VEGF as a Key Regulator of Embryo Implantation"; Endocrinology; 2011; p. 4948-4956; vol. 152, issue 12; The Endocrine Society.

Kobayashi et al.; "Superoxide Dismutase Activity in the Oviductal and Uterine Fluid of the Bitch and the Effects of the Enzyme on Viability, Motility and Hyperactivation of Canine Sperm In Vitro"; J. Vet. Med. Sci.; 2014; p. 741-743; vol. 76, issue 5.

Hamdi et al.; "Bovine oviductal and uterine fluid support in vitro embryo development"; Reproduction, Fertility and Development; 2017; 11 pages; CSIRO Publishing.

* cited by examiner

PROCESSING AND USE OF REPRODUCTIVE TRACT FLUIDS TO IMPROVE THE IN VITRO PRODUCTION OF MAMMALIAN EMBRYOS

OBJECT OF THE INVENTION

The present invention contemplates a method for increasing embryo quality by using the techniques of in vitro fertilization (IVF), optionally with a preincubation of oocytes in natural biological fluids of specific phases of the reproductive cycle, combined with a method of sperm processing in a culture supplemented with such fluids and the subsequent fertilization and embryo culture (EC) in media supplemented with fluids.

FIELD OF THE INVENTION

This invention belongs generally to the field of Assisted Reproduction in mammals, specifically sperm capacitation techniques, in vitro fertilization and embryo culture.

BACKGROUND AND STATE OF THE ART OF THE INVENTION

The procedure currently known for in vitro obtaining of an embryo involves making different assisted reproductive techniques (ART) that differ between laboratories and species, and comprises the following steps: 1) obtaining and in vitro maturation (IVM) of female gametes (oocytes); 2) the preparation and capacitation of male gametes (sperm); 3) the process of IVF itself either by co-culture of gametes or assisted microinjection of a sperm into the oocyte, and 4) the EC of the zygotes up to they reach the stage of desired development, usually the blastocyst stage.

A strategy to increase the efficiency of the ART has been to mimic in the laboratory the conditions that gametes-zygotes-embryos find in vivo where, after ovulation, the mature oocyte is captured by the oviduct (fallopian tubes) interacting with the natural medium, the oviductal fluid (OF). Meanwhile sperm "swim" from the vagina or cervix (depending on the species) to the site of fertilization (oviduct) contacting during its passage through the uterus with the uterine fluid (UF) and then, when they are already in near the oocyte, with the FO. Once both gametes are in the oviduct, fertilization and early embryonic development occur, being the OF the natural environment in which these reproductive events occur. Subsequently the embryo passes into the uterus, with the UF as the physiological medium where implantation and placentation will happen. Therefore, in order to develop and/or adapt new culture media employed in vitro, and to improve the current results of fertilization and embryo development, many studies have examined the composition of these natural fluids (Iritani et al. 1974, *J Anim Sci* 39: 582-588; Leese et al. 2008, *Reprod Fertil Dev* 20: 1-8). However, there have been no studies to reproduce in a combined and complete form the physiological environment designing systems a whole culture system (from IVF to EC) with culture media close to the composition of natural biological fluids (OF and UF). Even though, considering that it has been proven in humans that the addition to the culture medium of a "simple" oviductal protein increases more than 8% of births (Meintjes et al. 2009, *Hum Reprod* 24: 782-789).

Undoubtedly, the oviductal and uterine secretions provide better conditions for fertilization and embryonic development that conventional in vitro systems since the composition of these natural media varies along the different phases of the female reproductive cycle thus providing the oocyte, zygote and/or embryo the ideal conditions for their development at all times (Killian et al. 1989, *J Reprod Fertil.* 86: 419-426; Leese et al. 2008, *Reprod Fertil Dev* 20: 1-8). In general the natural biofluids contain salts, electrolytes, amino acids, protein and energy compounds. Among the more than 150 oviductal proteins that have been identified (Aviles et al 2010, *Mol Human Reprod* 16: 896-906), some are already commercially available and used as a supplement to the in vitro culture media (Hao et al. 2006, *Biol Reprod.* 75: 726-733; Meintjes et al. 2009, *Hum Reprod* 24: 782-789). However, the complete composition and exact concentration of all components of biofluids is unknown, so the direct addition of the biofluids to the artificial culture media is the cheapest, fast and reliable strategy to supplement them with all the compounds that gametes, zygotes and/or embryos needed in each of their development stages.

In mammals, including humans, the OF and/or UF are obtained by different techniques and are often processed with a single centrifugation and subsequent freezing of the liquid fraction (Carrasco et al. 2008a, *Reprod Fertil Dev* 20: 808-817; Carrasco et al. 2008b, *Reproduction* 136: 833-842; Faulkner et al. 2012, *Proteomics* 12: 2014-223; Lippes and Wagh 1993, *Fertil Steril* 59: 157-162; Velazquez et al 2010, *Theriogenology* 73: 758-767). These biofluids improve fertilization rates and increase embryo quality (Aitken 1977, *J Exp Embryol Morphol* 41: 295-300; Cebrian-Serrano et al. 2013, *Reprod Domest Anim* 48: 331-338; Coy et al. 2008a, *PNAS* 105 15809-15814; Lloyd et al. 2009, *Reproduction* 137: 679-687). Despite these encouraging results, to date the biofluids have not been used as additives in human ARTs which opens a new field of research, especially considering that, in most cases, the beneficial effect on gametes and embryos is interspecific, i.e. biofluids from a mammalian species can be used for ART in different species (Mondéjar et al. 2013, *Hum Reprod* 28: 718-728; Rondeau et al. 1996 can *J Vet Res* 60: 14-20). So far the processing, storage and transport of biofluids samples require a controlled temperature to maintain the cold chain, conditioning the implementation and extension of its use in the field of reproductive biology.

It has been described the beneficial effect of gametes contact with OF compounds before IVF (Coy et al. 2008b, *Reproduction* 135: 19-27; Coy et al. 2010, *Theriogenology* 74: 632-642) and it has been found that sperm processed by Swim-up technique show an increased DNA integrity and a lower percentage of morphological abnormalities than those obtained by Percoll method (Menkveld et al. 1990, *Andrology* 22: 152-158; Zini et al. 2000, *Urology* 56: 1081-1084). Although the process of sperm capacitation may seem a mere formality in the ART (it lasts only 45-60 minutes), the stress suffered by sperm is transmitted to offspring with metabolic and behavioural changes (Gapp et al. 2014, *Nat Neurosci* 17: 667-669).

It has been found 5 documents related to the use of specific substances in IVF and/or CE protocols but none of them describe the combined use of OF and UF from specific phases of the reproductive cycle in the generation of embryos. In these patents it is not described a purification or fractionation method of biofluids neither its use in sperm capacitation.

Patent-1 (ES 2 323 993 A1, Pilar Coy Fuster y Manuel Avilés Sánchez), where it is described a method to increase the monospermy during the IVF.

Patent-2 (ES 2 439 424 A1, Ignacio Santiago Alvarez Miguel y Mario Javier Perianes Carrasco), where it is described a method to increase the developmental potential of mammalian embryo obtained by IVF.

Patent-3 (WO2006/012177, Randall Prather): "Method to decrease the rate of polyspermy in IVF".

Patent-4 (US 2013/0344595 A1, David K. Gardner, Mark G. Larman y Donald Linck): "Culture media for developmental cells containing elevated concentrations of lipoic acid".

Patent-5 (CN103333855 (A), ZouXiangang y Zhao Yalin): "Sheep embryonic cell culture fluid".

DETAILED DESCRIPTION OF THE INVENTION

The present invention contemplates a method for increasing the quality of mammalian embryos obtained in vitro by a system that includes the addition of natural biological fluids (OF and/or UF) from specific phases of the reproductive cycle in the techniques of sperm capacitation, IVF and EC.

The authors of the present invention have developed on the one hand, a system for sperm capacitation that does not require centrifugation, where protein additive is OF and/or FU, which involves great advantages in reducing the stress that sperm cells are suffering during the process of separation of seminal plasma, and thus helps to select those sperm with better quality and DNA integrity. It has been managed to combine both strategies formulating a new culture medium for selecting sperm by Swim-up technique that offers better results than conventional procedures. On the other hand, it has carried out a new process for obtaining purified and lyophilized samples (dried) of both biofluids without losing their beneficial biological activity making thus possible to store dry samples that can be shipped at room temperature, what is an advantage against the conventional method used so far (liquid samples). All together increases the chances that this integrated system to obtain in vitro embryos can be implemented and developed in laboratories worldwide.

Currently, both the number and quality of mammalian embryos obtained through in vitro techniques are lower than that obtained in vivo. In the in vivo procedure, gametes contact with biofluid in isolation before fertilization and embryo development occur. So that, a complete protocol for obtaining high quality embryos should include this contact of gametes, in an individual way, with the biofluids; and replacing sperm selection systems such as Percoll (which involves centrifugation) by the swim-up technique where sperm swim freely.

The use of natural fluids that gametes and embryos specifically find in the reproductive tract along its development can increase the quality of embryos obtained in vitro. Thus, this invention proposes the introduction of these natural fluids of the reproductive tract, such as the OF and UF in the ARTs to improve the quality of embryos obtained in vitro. The invention describes a method for obtaining in vitro embryos by adding biofluids to the culture media in each of the stages of the process. The biofluids are obtained from genital tracts of mammalian females at specific phases of the reproductive cycle and are previously subjected to a process of purification and treatment for its preservation and transportation.

The invention comprises the following steps:
a) a method of classifying the OF and UF according to the stage of the reproductive cycle in which they are obtained, followed by double fractionation by centrifugation and subsequent processing by pasteurization and lyophilization.
b) a method of sperm capacitation without centrifugations in a specific culture medium supplemented with OF and/or UF.
c) IVF in a culture medium enriched with OF and/or UF.
d) in vitro culture and development of embryos obtained to any stage of development in media supplemented with OF and/or UF.

To carry out the fractionation method by double centrifugation and subsequent processing of biofluids by lyophilization, the OF and UF are obtained from animals slaughtered in the slaughterhouse (pig, swine, cattle, sheep, goat, rabbit and equine). Reproductive tracts are classified in the different phases of the estrous cycle: early follicular (F1), late follicular (F2), early luteal (L1) and late luteal (L2) according to the appearance and ovarian morphology (Carrasco et al 2008b, *Reproduction* 135: 19-27). In the human species biofluids are obtained from patients undergoing tubal ligation, hysterectomies or salpingectomy for health reasons and donors.

The OF is obtained by introducing the tip of an automatic pipette into the oviductal ampulla and exerting a manual pressure thus sucking all the oviductal content. For fractionation, the content is centrifuged (1-10 minutes, 4000-10000 g at 4° C.) and the cell pellet and mucosal phase is discarded. The supernatant of OF is recentrifuged under the same conditions being the aqueous phase at the top and the mucosal phase at the bottom of the tube. Only the aqueous phase of OF is drawn. Meanwhile, the UF is obtained by aspiration introducing the tip of an automatic pipette into the uterine horn and exerting an upward manual pressure. Such content is fractionated by a double centrifugation under the same conditions as the OF.

Once fractionated, biofluids are lyophilised at −60-−50° C. during 20-24 h at a pressure of 0.040-0.010 mbars. Once the process is finished, the biofluids are kept refrigerated until use. The biofluids obtained from the different species and phases of the cycle are stored in a biobank and can be used both in inter- or intraspecific manner as well as in autologous or heterologous way. Before being used as additives in a culture medium, the biofluids are resuspended with purified water to its original volume. One of the advantages of this new fractionation method is that biofluids can be transported at room temperature, retain their biological properties upon rehydration and can be pasteurized at 72-80° C. for 10-20 seconds before use, increasing the necessary sanitary warranties of the product.

The tests of the biological activity of the product have been performed to evaluate the ability of biofluids to harden the oocyte's zona pellucida (ZP) (Coy et al 2008b, *Reproduction* 135: 19-27). For that, mature oocytes were denuded and subjected to ZP digestion with a protease. The results show that biofluids subjected to fractionation and conservation process described in this patent retain their biological activity once they are resuspended and pasteurized.

For the development of sperm capacitation method without centrifugations and using media supplemented with biofluids, the present invention includes the formulation of a new culture medium for sperm selection that we call Swim-up-biofluids. To do this we rely on the media described in the literature (Alvarez et al. 1993, *Hum Reprod* 8: 1087-1092; Garcia-López et al. 1996, *J Chromatogr B Biomed Appl* 680: 137-143) but making the following changes on the composition:

Adjusting the salt concentration: within this group we include $NaHCO_3$, NaCl, KCl, $MgSO_4$, $K_2HPO_4$, and $CaCl_2$. They are responsible for maintaining the osmolarity and pH of the medium so that its concentration was adjusted to that described in the OF. The final osmolarity of the medium was kept in the physiological range of 280-320 mOsm. The concentration of inorganic salts was between 90 and 130 mM.

Adjusting pH: it was adjusted to 7.2-7.8 using HEPES as buffering agent to prevent pH oscillations in the medium during the time that sperm are in contact with it.

Adjusting the concentration of energy substrates: glucose, sodium pyruvate, sodium lactate and sucrose are within this group. Concentrations were adjusted to achieve optimal viscosity and density which allow the mobility of sperm through the medium. The concentration of energy substrates was between 120 and 160 mM.

Protein: in the new medium designed, Swim-up-biofluids, the protein source consisted of addition of 0.1-5% of phase F2-OF preferably fractionated and treated as described in step a). This treatment was compared with BSA (bovine serum albumin), the protein source commonly used in the culture media for sperm capacitation.

The capacitation method Swim-up-biofluids was performed by mixing 0.5-1.5 ml of semen with 0.5-1.5 ml of culture medium Swim-up-biofluids and allowing sperm to swim to the top of the tube for a time of 10-50 min at a temperature of 37-38° C. After this time, the top 0.5-1 ml was collected containing the sperm to be used for IVF. The new method of sperm capacitation was compared with the traditional method of centrifugation (Percoll; Matas et al 2003, Reproduction 125: 133-114). Thorough their research, the inventors have shown that when sperm are capacitated in the Swim-up-biofluids system using a culture medium supplemented with OF the monospermy rate is significantly improved and therefore the number of zygotes capable of developing up to embryo stage.

In the embodiment of IVF method including addition of biofluids to fertilization medium, the porcine oocytes are matured in vitro for 42-44 h according to protocols described (Coy et al. 2008b, Reproduction 135: 19-27). After that, cumulus-oocyte complexes are mechanically denuded and 50-55 oocytes are transferred to each well containing 500 ul of TALP medium for fertilization (control group) (Matas et al. 2003, Reproduction 125: 133-141) or TALP supplemented with 0.1-5% OF preferably from F2 or L1 phase, fractionated and treated as described in step a) (biofluids group). The sperm used for IVF were obtained and processed by Swim-up-biofluids system described in step b). Optionally, before being inseminated the denuded oocytes may be incubated in OF, preferably from F2 or L1 phase, for 30-60 minutes. Gametes were co-cultured for 18 hours and after this time the presumptive zygotes were fixed and stained to evaluate the results of fertilization. With this method monospermy rates are improved after fertilization.

In developing the EC in culture media supplemented with biofluids, the cumulus-oocyte complexes are matured according to the protocols described (Coy et al. 2008b, Reproduction 135: 19-27). Two methods of EC were compared, the control method and the biofluids method using fluids fractionated and treated as described in step a). For the biofluids group, sperm used for IVF were capacitated by Swim-up-biofluids method described in step b) and the oocytes were inseminated in culture medium supplemented with 0.1-5% OF, as described in step c). The obtained zygotes were transferred to embryo culture medium NCSU-23 (Petters and Wells 1993, J Reprod Fertility Suppl 48: 61-73) supplemented the first two to three days with 0.1-5% of OF, preferably from L1 or L2 phase. After the first 48 hours, cleavage was evaluated and then the divided embryos were transferred to NCSU-23 medium supplemented with 0.1-5% UF, preferably from L1 or L2 phase, up to the blastocyst stage. In the control group the biofluids were not used in any phase of the method, sperm were capacitated with Swim-up-BSA method, the oocytes were inseminated in TALP medium and zygotes were transferred to NCSU-23 for embryo culture. After culture period, the embryo quality in both groups was assessed attending to morphology (Bó and Mapletoft 2013, Anim Reprod 10: 344-348) and mean number of cells per blastocyst. Results show that embryos produced in vitro with the biofluids method divide faster than the control and are of better quality (evaluated as number of cells per blastocyst and ability to hatch).

Embodiment of the Invention

Method Used to Obtain In Vitro Derived-Embryos by Fertilization and Embryo Culture Using Biofluids from Different Stages of Reproductive Cycle and Checking the Improved Embryo Quality a.—Obtaining, Fractionation and Test of the Activity of the Biofluids In farm animals, OF and UF are obtained from genital tracts of animals slaughtered in a slaughterhouse for meat consumption. In the human species they can be obtained from donors, patients undergoing tubal ligation or women undergoing salpingectomy or hysterectomies for health reasons. The biofluids are centrifuged (4000-10000 g for 1-10 minutes at 4° C.) and the aqueous phase recentrifuged under the same conditions. This liquid is lyophilized and pasteurized being then ready for its use as an additive to culture media after resuspension with purified water. Treatment efficacy was estimated by the ability of OF to induce hardening of the oocyte's zona pellucida. For this, in vitro matured oocytes are mechanically denuded and incubated for 30-60 minutes in OF at 38.5° C. After this time the eggs are incubated with a 0.5% protease solution and the time it takes to digest the ZP is recorded. As shown in Table 1 the biofluids treated by our method maintained their biological activity with respect to untreated biofluids (control):

TABLE 1

Digestion time of the zona pellucida (ZP) of in vitro matured oocytes after being incubated 30-60 minutes in OF from phase F2, fractionated, lyophilized and pasteurized.

| Tratamiento del fluido oviductal | N | tdZP (seconds) |
|---|---|---|
| Control (non fractionated) | 14 | 3750.0 ± 665.2a |
| Fractionated | 14 | 7995.0 ± 70.8b |
| Fractionated and lyophilized | 14 | 9432.8 ± 534.2b |
| Fractionated, lyophilized and pasteurized | 10 | 8874.0 ± 445.6b |

Data are expressed as mean ± SEM.
Different letter indicate significant differences (P < 0.001)
N is the number of oocytes employed b.—Sperm Capacitation without Centrifugations in a New Culture Medium Enriched with Biofluids The new culture medium was formulated by adjusting the osmolarity, pH and energy substrates and replacing bovine serum albumin (BSA) by biofluids. The capacitation was performed with ejaculated sperm from proven fertility males (12-24 months old). For the capacitation with Swim-up-biofluids method, semen was deposited on Swim-up-biofluids medium for 15-30 minutes at 37-38° C. After this time the sperm cells were collected from the top and sperm concentration was adjusted to 25.000 sperm/ml using with TALP culture medium (Matas et al. 2003, Reproduction 125: 133-114). This new method of sperm capacitation was compared with the traditional method of centrifugation (Percoll) (Matas et al. 2003, Reproduction 125: 133-114). The quality of the obtained sperm was assessed by their ability to fertilize porcine oocytes previously matured in vitro for 42-44 hours according to standard protocols (Coy et al. 2008b, Reproduction 135: 19-27). Oocytes were cocultured for 18 hours with spermatozoa capacitated in the different methods. After this time the presumptive zygotes were fixed and stained to evaluate the fertilization results (Coy et al. 2008b, 135 Reproduction: 19-27). The results showed that sperm capacitated with the Swim-up-biofluids system with medium supplemented with OF significantly improve monospermy by reducing the number of sperm binding to the zona pellucida of the oocyte (SPZ/ZP) and number of sperm penetrating into the oocyte (SPZ/OO), thereby obtaining higher performance (YIE) of the technique than with the conventional centrifugations system as shown in table 2.

TABLE 2

IVF results after capacitation of sperm in a traditional method with centrifugations (Percoll) or a method without centrifugations with a new culture medium in which it has been used as a protein source albumin (Swim-up-BSA) or the biofluids (Swim-up-biofluids). PEN (percentage of penetrated oocytes), MONO (percentage of monospermy), SPZ/OO (average number of spermatozoa per penetrated oocyte), SPZ/ZP (average number of sperm bound to the zona pellucida) and YIE (yield, percentage of viable zygotes from the total penetrated).

| Capacitation method | N | PEN (%) | MONO (%) | SPZ/OO | SPZ/ZP | YIE (%) |
|---|---|---|---|---|---|---|
| Percoll | 105 | 84.3 ± 3.6a | 17.4 ± 4.1a | 8.4 ± 0.7a | 17.3 ± 2.3a | 14.6 ± 0.1a |
| Swim-up-BSA | 180 | 69.6 ± 3.5b | 42.7 ± 4.6ab | 2.1 ± 0.1b | 7.2 ± 0.5b | 29.7 ± 0.2b |
| Swim-up-biofluids | 183 | 71.1 ± 3.4b | 49.6 ± 4.5b | 2.7 ± 0.1b | 8.6 ± 0.5b | 35.2 ± 0.2c |

The data are expressed as mean ± SEM.
Different letters indicate significant differences (P < 0.05).
N is the number of inseminated oocytes c.—Obtaining of Embryos by IVF in Media Supplemented with Biofluids Once the sperm are capacitated with the swim-up-biofluids system, IVF is performed in a culture medium (TALP) with or without biofluids. Oocytes are matured under standard protocols described above and transferred to fertilization medium. The results of this invention have shown that when the oocytes are inseminated in a culture medium supplemented with OF penetration rates are increased and high levels of monospermy remain (Table 3). This makes the performance (YIE) of the IVF with the biofluids method is significantly higher yielding a greater number of putative embryos.

TABLE 3

IVF results after supplementing the fertilization medium with biofluids. PEN (percentage of penetrated oocytes), MONO (percentage of monospermy), SPZ/OO (average number of spermatozoa per penetrated egg), SPZ/ZP (average number of sperm bound to the zona pellucida) and YIE (yield, percentage of viable zygotes from the total penetrated).

| Capacitation methods | N | PEN (%) | MONO (%) | SPZ/OO | SPZ/ZP | YIE (%) |
|---|---|---|---|---|---|---|
| Control | 32 | 43.7 ± 0.1a | 78.6 ± 0.1 | 1.2 ± 0.1 | 13.4 ± 2.1 | 34.4 ± 0.1a |
| Biofluids | 33 | 66.6 ± 0.1b | 72.7 ± 0.1 | 1.3 ± 0.1 | 19.3 ± 3.2 | 48.5 ± 0.1b |

Data are expressed as mean ± SEM.
Different letters indicate significant differences at P < 0.05.
N is the number of inseminated oocytes d.—Embryo Culture with Biofluids and Assessment of the Quality of Obtained Embryos After the fertilization period, zygotes were transferred to culture medium (NCSU-23) supplemented or not with OF from early luteal phase for 48 hours where they were cultured until 2-4 cells stage. After this time the embryos were transferred to NCSU-23 medium supplemented or not with UF from early luteal phase where they were culture up to the blastocyst stage. To check the effects of biofluids system on embryo quality parameters such as cleavage, number of blastocysts at each stage of development (from early blastocyst to hatched blastocyst), average number of cells per blastocyst and its functionality, evaluated as their ability to hatch (expand and contract rhythmically to get out of the zona pellucida), were assessed. It was found that embryos obtained by biofluids system had significantly better quality than the embryos that had not been in contact with these natural fluids, as evidenced by the increased number of cells per blastocyst (Table 4) and the highest percentage of blastocysts that initiate and complete the process of hatching (Table 5).

TABLE 4

Results of embryo culture with biofluids method.

| Group | N | Cleavage (%) | Blastocyst formation (%)* | YIE (%) | Cells/blastocyst |
|---|---|---|---|---|---|
| Control | 903 | 47.5 ± 1.6a | 41.4 ± 2.4 | 19.6 ± 1.3 | 49.9 ± 3.7a |
| Biofluids | 961 | 42.1 ± 1.6b | 44.5 ± 2.5 | 18.7 ± 1.2 | 81.8 ± 7.2b |

Data are expressed as mean ± SEM.
Different letters indicate significant differences at P < 0.05.
YIE (method performance, blastocyst rate with respect to embryos divided).
*With respect to embryos divided.
N is the number of employed zygotes

TABLE 5

Developemenatl stage of blastocysts (Blasto) obtained in vitro with biofluids method.

| Group | N | Early blasto | Blasto | Expand blasto | Hatching blasto | Hatched blasto |
|---|---|---|---|---|---|---|
| Control | 903 | 31.7 ± 6.1a | 28.3 ± 5.9 | 40.0 ± 6.4 | 0a | 0a |
| Biofluido | 961 | 12.8 ± 5.4b | 30.8 ± 7.5 | 35.9 ± 7.8 | 15.4 ± 5.9b | 5.1 ± 3.6b |

Data are expressed as mean ± SEM.
Different letters indicate significant differences at $P < 0.05$.
N is the number of employed zygotes When it is compared the average number of cells from in vitro-derived blastocysts with in vivo-derived blastocyst, it is observed that the number of cells of the embryos obtained with biofluids method is similar to in vivo embryos, while the control method have about half cells (Table 6). This result shows that quality of embryos obtained with the biofluids method is similar to that obtained naturally, at least regarding this quality parameter.

TABLE 6

Average number of cells per blastocyst obtained in vivo and in vitro with the control and biofluids methods.

| Method | Cells/blastocyst |
|---|---|
| Control | 49.9 ± 3.6a |
| Biofluids | 81.8 ± 7.2b |
| In vivo | 87.0 ± 7.2b |

Data are expressed as mean ± SEM.
Different letters indicate significant differences with $P < 0.001$.

The invention claimed is:

1. A method of using biofluids characterized by the steps of:
   i) classifying oviductal fluid and uterine fluid based on a stage of estrous cycle in which the oviductal fluid and the uterine fluid were obtained, wherein the stage of estrous cycle is selected from the group consisting of: early follicular (F1), late follicular (F2), early luteal (L1), and late luteal (L2), wherein the classifying yields one or more of the following: an F1 oviductal fluid, an F1 uterine fluid, an F2 oviductal fluid, an F2 uterine fluid, an L1 oviductal fluid, an L1 uterine fluid, an L2 oviductal fluid, and an L2 uterine fluid;
   ii) fractionating each of the oviductal fluids and the uterine fluids classified in step i) independently by twice centrifugation, wherein the twice centrifugation comprises:
      centrifuging the F1 oviductal fluid, the F1 uterine fluid, the F2 oviductal fluid, the F2 uterine fluid, the L1 oviductal fluid, the L1 uterine fluid, the L2 oviductal fluid, and/or the L2 uterine fluid to separate a pellet from a supernatant;
      discarding the pellet;
      centrifuging the supernatant to separate out an aqueous phase of the F1 oviductal fluid, the F1 uterine fluid, the F2 oviductal fluid, the F2 uterine fluid, the L1 oviductal fluid, the L1 uterine fluid, the L2 oviductal fluid, and/or the L2 uterine fluid after discarding a mucosal phase; and
      collecting the aqueous phase of the F1 oviductal fluid, the F1 uterine fluid, the F2 oviductal fluid, the F2 uterine fluid, the L1 oviductal fluid, the L1 uterine fluid, the L2 oviductal fluid, and/or the L2 uterine fluid;
   iii) improving sperm functionality by adding the aqueous phase of the F2 oviductal fluid to a culture medium, processing a seminal sample in the culture medium, selecting sperm based on physiological ability to swim freely through the culture medium, and collecting the selected sperm;
   iv) in vitro fertilizing an oocyte using the sperm collected in step iii) to obtain a zygote in a medium supplemented with the aqueous phase of the F2 oviductal fluid or the aqueous phase of the L1 oviductal fluid;
   v) transferring the zygote obtained in step iv) to a culture medium supplemented 24 to 72 hours from fertilization with the aqueous phase of the L1 oviductal fluid or the aqueous phase of the L2 oviductal fluid; and
   vi) transferring a resulting embryo (4-16 cell stage) to a culture medium supplemented 72 or more hours with the aqueous phase of the L1 uterine fluid or the aqueous phase of the L2 uterine fluid, up to a blastocyst stage.

* * * * *